United States Patent [19]

Cerretti et al.

[11] Patent Number: 5,171,675
[45] Date of Patent: Dec. 15, 1992

[54] MACROPHAGE COLONY STIMULATING FACTOR-γ

[76] Inventors: Douglas P. Cerretti, 1607 N. 197th Pl.; Dirk M. Anderson, 16612 Wallingford Ave. North, both of Seattle, Wash. 98133; Robert J. Tushinski, 1402 NW. Woodbine Way, Seattle, Wash. 98177; Byron M. Gallis, 310 Blain Street, Seattle, Wash. 98109; David Cosman, 116 11th Ave. NE., #501, Seattle, Wash. 98102

[21] Appl. No.: 391,218

[22] Filed: Aug. 8, 1989

Related U.S. Application Data

[63] Continuation of Ser. No. 226,050, Jul. 28, 1988, abandoned.

[51] Int. Cl.$^5$ .................. C12P 21/02; C07K 13/00; C12N 15/27
[52] U.S. Cl. .................. 435/69.5; 435/320.1; 530/399; 536/27
[58] Field of Search .................. 435/69.5, 320.1; 536/27

[56] References Cited

FOREIGN PATENT DOCUMENTS 0272779  6/1988  European Pat. Off. .
8604587  8/1986  PCT Int'l Appl. .
8604607  8/1986  PCT Int'l Appl. .
8706954  11/1987 PCT Int'l Appl. .

OTHER PUBLICATIONS

Mount, *Nuc. Acids Res.* v. 10, 1982, pp. 459–472.
Das et al., "Human CSF-1 Radioimmunoassay: Resolution of Three Subclasses of Human CSFs," *Blood* 58:630–641 (1981).
Waheed and Shadduck, "A Rapid Technique for the Purification of Human Urinary CSF," *Exp. Hematol.* 12:434 (1984).
Stanley and Heard, "Factors Regulating Macrophage Production and Growth . . . . " *J. Biol. Chem.* 252:4305–4312 (1977).
Wang and Goldwasser, "Purification of a Human Urinary Colony-Stimulating Factor," *J. Cell Biochem.* 21:263 (1983).
Kawasaki et al., "Molecular Cloning of a Complementary DNA Encoding Human Macrophage-Specific Colony-Stimulating Factor (CSF-1)", *Science* 230: 291–296 (1985).
Wong et al., "Human CSF-1: Molecular Cloning and Expression of a 4-kb cDNA Encoding the Human Urinary Protein," *Science* 235:1504–1508 (1987).

*Primary Examiner*—Richard A. Schwartz
*Assistant Examiner*—James S. Ketter
*Attorney, Agent, or Firm*—Christopher L. Wight

[57] ABSTRACT

A macrophage colony stimulating factor, M-CSFγ, which is a primary translation product of an alternative mRNA splicing event and is a precursor to biologically active M-CSF. DNA sequences encoding M-CSFγ and recombinant expression vectors comprising the DNA sequences.

18 Claims, 6 Drawing Sheets

Figure 2

```
Met Thr Ala Pro Gly Ala Ala Gly Arg Cys Pro Pro Thr Thr Trp Leu Gly Ser Leu Leu Leu Leu Val Cys Leu Leu Ala Ser Arg Ser    30
ATG ACC GCG CCG GGC GCC GGG CGC TGC CCT CCC ACG ACA TGG CTG GGC TCC CTG CTC CTG TTG CTC CTG GTC TGT CTC CTG GCG AGC AGT     90

Ile Thr Glu Glu Val Ser Glu Tyr Cys Ser His Met Ile Gly Ser Gly His Leu Gln Ser Leu Gln Arg Leu Ile Asp Ser Gln Met Glu    60
ATC ACC GAG GAG GTG TCG GAG TAC TGT AGC CAC ATG ATT GGG AGT GGG CAC CTG CAG TCT CTG CAG CGG CTG ATT GAC AGT CAG ATG GAG    180

Thr Ser Cys Gln Ile Thr Phe Glu Phe Val Asp Gln Glu Gln Leu Lys Asp Pro Val Cys Tyr Leu Lys Lys Ala Phe Leu Leu Val Gln    90
ACC TCG TGC CAA ATT ACA TTT GAG TTT GTA GAC CAG GAA CAG TTG AAA GAT CCA GTG TGC TAC CTT AAG AAG GCA TTT CTC CTG GTA CAA    270

Tyr Ile Met Glu Asp Thr Met Arg Phe Arg Asp Asn Thr Pro Asn Ala Ile Ala Ile Val Gln Leu Gln Glu Leu Ser Leu Arg Leu Lys   120
TAC ATA ATG GAG GAC ACC ATG AGA TTC CGA GAT AAC ACC CCC AAT GCC ATC GCC ATT GTG CAG CTG CAA GAA CTC TCT TTG AGG CTG AAG    360

Ser Cys Phe Thr Lys Asp Tyr Glu Glu His Asp Lys Ala Cys Val Arg Thr Phe Tyr Glu Thr Pro Leu Gln Leu Leu Glu Lys Val Lys   150
AGC TGC TTC ACC AAG GAT TAT GAA GAG CAT GAC AAG GCC TGC GTC CGA ACT TTC TAT GAG ACA CCT CTC CAG TTG CTG GAG AAG GTC AAG    450

Asn Val Phe Asn Glu Thr Lys Asn Leu Leu Asp Lys Asp Trp Asn Ile Phe Ser Lys Asn Cys Asn Asn Ser Phe Ala Glu Cys Ser Ser   180
AAT GTC TTT AAT GAA ACA AAG AAT CTC CTT GAC AAG GAC TGG AAT ATT TTC AGC AAG AAC TGC AAC AAC AGC TTT GCT GAA TGC TCC AGC    540

Gln Asp Val Val Thr Lys Pro Asp Cys Asn Cys Leu Tyr Pro Lys Ala Ile Pro Ser Ser Asp Pro Ala Ser Val Ser Pro His Gln Pro   210
CAA GAT GTG GTG ACC AAG CCT GAT TGC AAC TGC CTC TAC CCC AAA GCC ATC CCT TCT AGT GAC CCT GCC TCT GTC TCC CCT CAT CAG CCC    630

Leu Ala Pro Ser Met Ala Pro Val Ala Gly Leu Thr Trp Glu Asp Ser Glu Gly Thr Glu Gly Ser Ser Leu Leu Pro Gly Glu Gln Pro   240
CTC GCC CCC TCC ATG GCT CCT GTG GCT GGC TTG ACC TGG GAG GAC TCT GAG GGA ACT GAG GGC AGC TCC CTC CTT CCT GGT GAG CAG CCC    720

Leu His Thr Val Asp Pro Gly Ser Ala Lys Gln Arg Pro Pro Arg Ser Thr Cys Gln Ser Phe Glu Pro Pro Glu Thr Pro Val Val Lys   270
CTG CAC ACA GTG GAT CCA GGC AGT GCC AAG CAG CGG CCT CCA AGG AGC ACC TGC CAG AGC TTT GAG CCG CCA GAG ACC CCA GTT GTC AAG    810

Asp Ser Thr Ile Gly Gly Ser Pro Gln Pro Arg Pro Ser Val Gly Ala Phe Asn Pro Gly Met Glu Asp Ile Leu Asp Ser Ala Met Gly   300
GAC AGC ACC ATC GGT GGT TCA CCA CAG CCT CGC CCC TCT GTC GGC GCC TTC AAC CCC GGG ATG GAG GAT ATT CTT GAC TCT GCA ATG GGC    900

Thr Asn Trp Val Pro Glu Glu Ala Ser Gly Glu Ala Ser Glu Ile Pro Val Pro Gln Gly Thr Glu Leu Ser Pro Ser Arg Pro Gly Gly   330
ACT AAT TGG GTC CCA GAA GAA GCC TCT GGA GAA GCC AGT GAG ATT CCC GTA CCC CAA GGA ACA GAG CTT TCC CCA TCC AGG CCA GGA GGG    990
```

```
Gly Ser Met Gln Thr Glu Pro Ala Arg Pro Ser Asn Phe Leu Ser Ala Ser Pro Leu Pro Ala Ser Ala Lys Gly Gln Gln Pro Ala   360
GCC AGC ATG CAG ACA GAG CCC GCC AGA CCC AGC AAC TTC CTC TCA GCA TCT CCA CTC CCT GCA TCA GCA AAG GGC CAA CAG CCG GCA  1080

Asp Val Thr Ala Leu Pro Arg Val Gly Pro Thr Gly Gln Asp Trp Asn His Thr Pro Gln Lys Thr Asp His Pro                  390
GAT GTA ACT GCC TTG CCC AGG GTG GGC CCC ACT GGC CAG GAC TGG AAT CAC ACC CCC CAG AAG ACA GAC CAT CCA                  1170

Ser Ala Leu Leu Arg Asp Pro Pro Glu Pro Arg Ile Ser Leu Arg Ser Leu Arg Ser Asn Pro Ser Thr Leu Ser                  420
TCT GCC CTG CTG AGA GAC CCT CCC GAG CCC AGA ATC TCA TCA CGG AGC CTC AGC AAC CCC TCC ACC CTC TCT                      1260

Ala Gln Pro Gln Leu Ser Arg Ser His Ser Ser Gly Ser Val Leu Pro Leu Gly Glu Leu Glu Gly Arg Arg Ser Thr Arg Asp Arg Arg   450
GCT CAG CCA CAG CTT TCC AGA AGC CAC AGC TCC GGC AGC GTG CTT CCC CTT GGG GAG CTG GAG GGC AGG AGA AGC ACC AGG GAT CGG AGG  1350

Ser Pro Ala Glu Gly Leu Pro Glu Gly Gly Ala Ser Glu Ala Ala Arg Phe Asn Ser Val Pro Leu Thr Asp Thr Gly             480
AGC CCC GCA GAG GGA CTA CCA GAA GGG GGC GCA AGT GAA GCA GCA AGG TTT AAC TCC GTT CCT TTG ACT GAC ACA GGC             1440

His Glu Arg Gln Ser Glu Gly Gly Ser Ser Ser Pro Gln Leu Gln Glu Ser Val Phe His Leu Leu Val Pro Ser Val Ile Leu Val Leu Leu   510
CAT GAG AGG CAG AGC GAG GGA GGT TCC TCC AGC CCG CAG CTC CAG GAG TCT GTC TTC CAC CTG CTG GTC CCC AGT GTC ATC CTG GTG TTG CTG  1530

Ala Val Gly Gly Leu Leu Phe Tyr Arg Trp Arg Arg Arg Ser His Gln Glu Pro Gln Arg Ala Asp Ser Pro Leu Glu Gln Pro Glu Gly       540
GCC GTC GGA GGC CTC TTG TTC TAC AGG TGG CGG AGA CGG AGC CAT CAA GAG CCT CAG AGA GCC GAT TCT CCC CTT GAG CAA CCA GAG GGC       1620

Ser Pro Leu Thr Gln Asp Asp Arg Gln Val Glu Leu Pro Val End                                                         554
AGC CCC CTG ACT CAG GAT GAC CGG CAG GTG GAA CTG CCA GTG TAG                                                         1665
```

Figure 2 (continued)

Biological Activity of Human M-CSF

| Plasmids | Murine Bone Marrow Assays | | Human Bone Marrow Assays | | | |
|---|---|---|---|---|---|---|
| | Proliferation (U/ml) | Colonies (CFU-C/ml) | Proliferation (u/ml) | Colonies* (CFU-C/ml) | | |
| | | | | Assay 1 | Assay 2 | Assay 3 |
| pDC201 | 0 | 0 | 0 | 43 | 0 | 0 |
| pDCCSFα | 3177 | 19,140 | 0 | 1530 | 238 | 315 |
| pDCCSFβ | 5375 | 35,863 | 0 | 4930 | 280 | 2163 |
| pDCCSFγ | 3991 | 16,240 | 0 | 1912 | 392 | 1008 |
| pDC[s]CSFα | 16,443 | 114,260 | 0 | 553 | 1092 | 789 |
| pMLSV | 63 | 1815 | 0 | 320 | 120 | — |
| genomic-CSF-1** | | | | | | |
| rGM-CSF*** | 0 | 0 | 130,876 | 459,963 | 111,531 | 520,304 |

\* Assays 1,2 and 3 represent bone marrow from three donors.
\*\* These assays were done on separate days.
\*\*\* Purified recombinant human GM-CSF at 1 μg/ml.

Figure 5

MACROPHAGE COLONY STIMULATING FACTOR-γ

CROSS-REFERENCE TO RELATED APPLICATION

This application is a continuation of U.S. Ser. No. 07/226,050, filed Jul. 28, 1988, now abandoned.

BACKGROUND OF THE INVENTION

The present invention relates to macrophage colony stimulating factors (M-CSF) and, more specifically, to macrophage colony stimulating factor-γ (M-CSFγ).

Colony stimulating factors are proteins that influence the growth and differentiation of cells responsible for the formation of blood in the body and have traditionally been defined by their ability to stimulate growth of colonies of bone marrow cells in semi-solid media. Macrophage colony stimulating factor ("M-CSF") is a subclass of colony stimulating factors and plays a role in the regulation of immune responses by potentiating the proliferation and differentiation of macrophages from immature hematopoietic progenitor cells, and inducing effector functions of mature macrophages including secretion of interferon-γ, tumor necrosis factor and non-M-CSF colony stimulating activities. Native mammalian M-CSF is a glycosylated, disulfide-linked homodimer with molecular weights ranging from 45 to 90 kilodaltons (kDa). Disulfide bond formation is required for biological activity.

Recently, two human M-CSF complementary DNAs (cDNA) encoding distinct M-CSF proteins have been isolated. Kawasaki et al. (Science 230:291, 1985) first reported the isolation of a cDNA clone from a human pancreatic carcinoma cell line, MIA-PaCa. This cDNA, when expressed in COS-7 cells, produced M-CSF activity as judged by its ability to cause proliferation and monocytic colony formation from murine bone marrow cells. The cDNA encoded a protein of 256 amino acids that included a 32 amino acid signal sequence and a putative transmembrane region of 23 hydrophobic amino acids near its carboxyl end. It was proposed that this protein was synthesized as a membrane-bound precursor that was then proteolytically cleaved, releasing mature M-CSF.

A second M-CSF cDNA was isolated by Wong et al. (Science 235:1504, 1987), who reported that this cDNA encoded a protein of 554 amino acids. The larger coding region was due to an in-frame insertion of 894 bp after amino acid 181. The coding regions from both cDNAs share the same amino- and carboxyl-terminal amino acids including the signal sequence and transmembrane regions. The larger cDNA, upon expression in COS-7 cells, was found to yield a biologically active protein as judged by its ability to form monocytic colonies from human and murine bone marrow cells. It was suggested that the two M-CSF cDNAs were formed by alternate splicing of mRNA. In order to distinguish the two distinct proteins identified and isolated by Kawasaki et al. and Wong et al., they are referred to herein as M-CSFα and M-CSFβ, respectively.

The existence of several distinct but related species of M-CSF now raises the possibility that these and possibly other different forms may be responsible for mediating the different biological activities described above. In order to fully elucidate the biological role of M-CSF activity, it is thus necessary to identify and characterize the factors responsible for M-CSF activity.

SUMMARY OF THE INVENTION

The present invention is directed to yet a third species of M-CSF, designated herein as M-CSFγ. In one aspect of the invention, a DNA sequence is provided comprising a single open reading frame nucleotide sequence encoding human M-CSFγ. Preferably, such DNA sequences are selected from the group consisting of (a) cDNA clones having the nucleotide sequence of FIG. 2; (b) DNA sequences capable of hybridization to the clones of (a) under moderately stringent conditions and which encode M-CSFγ molecules; and (c) DNA sequences which are degenerate as a result of the genetic code to the DNA sequences defined in (a) and (b) and which encode M-CSFγ. The present invention also provides recombinant expression vectors comprising the DNA sequences defined above, and recombinant M-CSFγ molecules produced using the recombinant expression vectors.

In another aspect of the present invention, homogeneous human M-CSFγ protein compositions are provided having a molecular size of about 44 kilodaltons (kDa).

These and other aspects of the present invention will become evident upon reference to the following detailed description and attached drawings.

BRIEF DESCRIPTION OF THE DRAWINGS

FIG. 2 represents the cDNA sequence of the M-CSF cDNA clones, M-CSFα, M-CSFβ and M-CSFγ. Deletion of sequence between arrows #1 would result in M-CSFα and deletion of sequence between arrows #2 would result in M-CSFγ. The star indicates the amino-terminus of mature M-CSF, boxed regions indicate potential N-linked glycosylation sites, and the underlined sequence indicates the membrane spanning region. The triangle represents the 5' end of the M-CSFγ cDNA isolate, λ-8.

FIG. 5 is a table showing biological activity of human M-CSF. Supernatants from COS-7 cells transfected with M-CSF expression plasmids, and concentrated approximately five fold by Amicon filtration, were analyzed for biological activity using both human and murine bone marrow cells (see Example 6). The results are expressed in either units/ml for proliferation of CFU-C/ml for the colony assays. Human colony assays were carried out using marrow from three different donors. The data shown represent the average of triplicates assays, all of which had a standard deviation of ≦10% of stated values.

DETAILED DESCRIPTION OF THE INVENTION

Definitions

Figure 1:
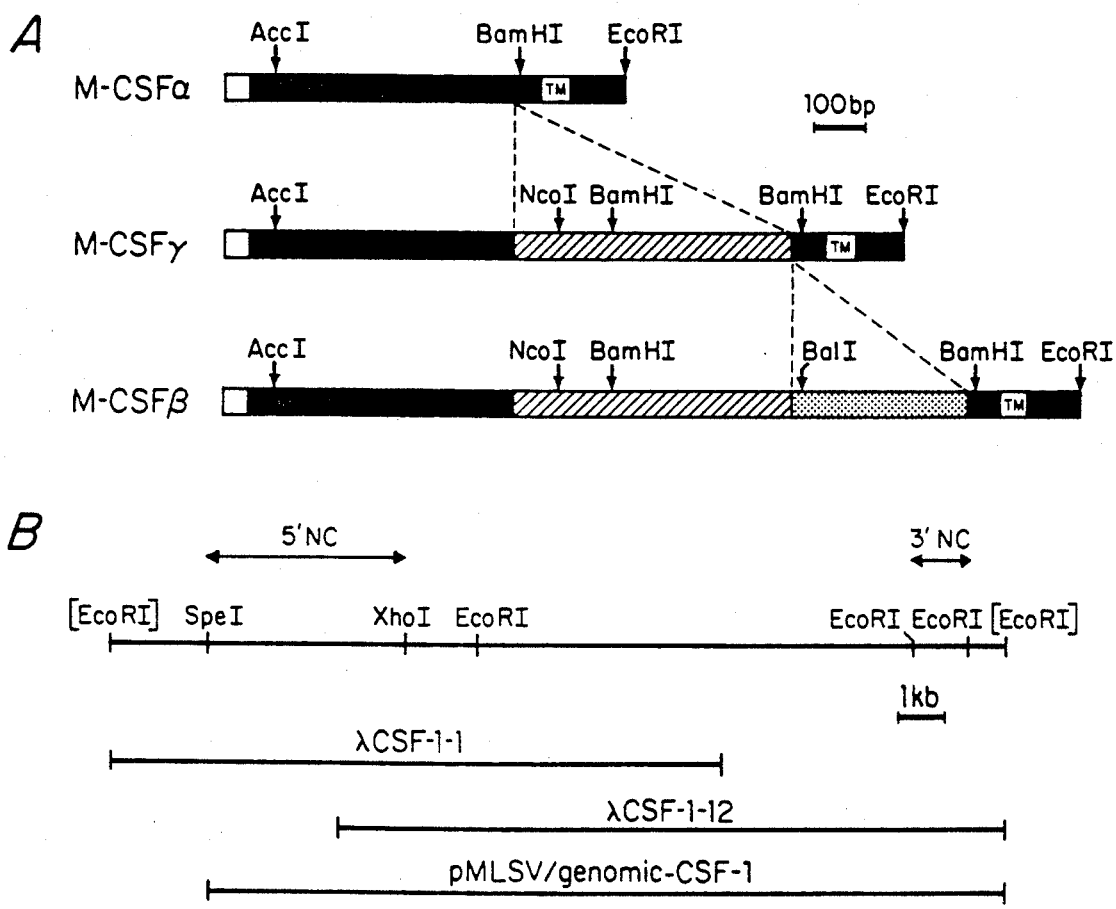
FIG. 1A shows partial restriction endonuclease maps of the human M-CSF cDNAs M-CSFα, M-CSFβ, and M-CSFγ. Boxed regions indicate coding sequences; open boxes (signal sequences), closed boxes and transmembrane boxes (TM) are common to all three M-CSF cDNA clones. The striped boxes represent sequences common to M-CSFβ and M-CSFγ and the stippled box represents coding sequence unique to M-CSFβ.
FIG. 1B shows a partial restriction endonuclease map of the gene for human M-CSF. The size of the genomic sequences in the λ-phage clones, λCSF-1-1 and λCSF-1-12, and in the mammalian expression vector, pMLSV/genomic-CSF-1, are indicated. 5' NCD and 3' NC represent the restriction fragments that hybridize to the 5'-noncoding region probe and the 3'-noncoding region probe of M-CSFα, respectively, in Southern blot analysis.

"Macrophage colony stimulating factor" and "M-CSF" refer to a protein capable of inducing biological activity as defined by the ability of transfected COS cell supernatants to stimulate proliferation and colony formation of murine bone marrow cells, as well as formation of monocytic colonies from human bone marrow cells. The particular assays used for this determination are set forth below in Example 6.

"M-CSFγ" refers to a protein which is a 438 amino acid precursor to M-CSF and is a primary translation product of an alternative mRNA splicing event. After translation, M-CSFγ is inserted into the plasma membrane and cleaved, releasing a soluble biologically active M-CSF monomer subunit protein of about 44 kDa. M-CSFγ has an amino acid sequence as set forth in FIG. 2. Prior to being inserted into the plasma membrane, M-CSFγ has a theoretical molecular weight of 47,890 including the leader sequence; without the leader sequence, the theoretical molecular weight is 44,638.

"Substantially identical" and "substantially similar," when used to define amino acid sequences, mean that a particular subject sequence, for example, a mutant sequence, varies from a reference sequence by one or more substitutions, deletions, or additions, the net effect of which does not result in an adverse functional dissimilarity between reference and subject sequences. For purposes of the present invention, amino acid sequences having greater than 30 percent similarity are considered to be substantially similar, and amino acid sequences having greater than 80 percent similarity are considered to be substantially identical. In defining nucleic acid sequences, all subject nucleic acid sequences capable of encoding substantially similar amino acid sequences are considered substantially similar to a reference nucleic acid sequence, and all nucleic acid sequences capable of encoding substantially identical amino acid sequences are considered substantially identical to a reference sequence. For purposes of determining similarity, truncation or internal deletions of the reference sequence should be disregarded. Sequences having lesser degrees of similarity, comparable biological activity, and equivalent expression characteristics are considered to be equivalents.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein essentially free of native endogenous substances and unaccompanied by associated native glycosylation. Protein expressed in most bacterial cultures, e.g., *E. coli*, will be free of glycan; protein expressed in yeast will have a glycosylation pattern different from that expressed in mammalian cells.

"Biologically active," as used throughout the specification as a characteristic of M-CSF, means either that a particular molecule shares sufficient amino acid sequence similarity with the embodiments of the present invention disclosed herein to be capable of causing proliferation of monocytic colony formation in murine bone marrow cells and forming monocytic colonies from human bone marrow cells.

"DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes (i.e., a single open reading frame nucleotide sequence). However, it will be evident that genomic DNA containing the relevant sequences could also be used. Sequences of non-translated DNA may be present 5' or 3' from the open reading frame, where the same do not interfere with manipulation or expression of the coding regions. "Nucleotide sequence" refers to a heteropolymer of deoxyribonucleotides. DNA sequences encoding the proteins provided by this invention are assembled from cDNA fragments and short oligonucleotide linkers, or from a series of oligonucleotides, to provide a synthetic gene which is capable of being expressed in a recombinant transcriptional unit.

"Recombinant expression vector" refers to a plasmid comprising a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

"Recombinant microbial expression system" means a substantially homogeneous monoculture of suitable host microorganisms, for example, bacteria such as *E. coli* or yeast such as *S. cerevisiae*, which have stably integrated a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

The synthesis of human M-CSF is more complex than the other hematopoietic growth factors. The gene for M-CSF transcribes multiple RNA species that range in size from 1.5 to 4.4 kb. After translation, M-CSF polypeptides are glycosylated, react with each other to form dimers and are inserted into the plasma membrane. The membrane-bound precursor is then cleaved, releasing secreted M-CSF. The two known cDNAs that encode biologically active M-CSF, namely M-CSFα and M-CSFβ, encode proteins of 256 and 554 amino acids, respectively. M-CSFγ of the present invention encodes a protein of 438 amino acids. While not being bound to any particular theory, it is believed that the cDNAs are likely a result of alternative RNA splicing within the coding region of the gene as judged by the presence of consensus splice sequences at the divergence points between the cDNAs. It is possible that the M-CSFβ mRNA could be spliced to give either the M-CSFα or M-CSFγ mRNAs by using alternative donor sites spliced to the same acceptor site. Alternatively, all three mRNAs could be produced by alternative splicing of a common precursor. The proteins encoded by M-CSFα, M-CSFβ and M-CSFγ have a common amino terminus of 149 amino acids including a 32 amino acid signal sequence and a common 75 amino acid carboxyl-terminus including a membrane-spanning region. Each of the M-CSF molecules is represented by a form anchored to the plasma membrane. M-CSFβ and M-CSFγ have an additional 298 and 182 amino acids, respectively, as compared to M-CSFα. This insertion is upstream and adjacent to the membrane spanning region. It is within this region that the membrane-bound precursors are likely to be proteolytically processed.

Isolation of cDNAs Encoding M-CSFγ

In order to identify the coding sequence of human M-CSFγ, a DNA sequence encoding human M-CSFγ was isolated from a cDNA library prepared by reverse transcription of polyadenylated mRNA isolated from mitogen-stimulated human pancreatic tumor cells, MIA-PaCa-2, which are known to produce significant levels of human M-CSF. The library was probed with an M-CSF probe ([s]M-CSFα) consisting of nucleotides 97 to 544 and 1439 to 1467 (FIG. 2). This fragment was assembled from 16 synthetic oligonucleotides and contains the first 158 amino acids of M-CSFα. Restriction mapping and DNA sequence analysis of eight hybridizing clones revealed three classes of M-CSF cDNAs (FIGS. 1A and 2). Two of the classes represent the M-CSFα (three isolates) and M-CSFβ (four isolates) cDNAs isolated previously by Kawaski et al. and Wong et al. However, a new class of M-CSF cDNA, referred to here as M-CSFγ (one isolate), was found that encodes a primary translation product intermediate in size to M-CSFα and M-CSFβ.

The M-CSFγ cDNA encoded a protein of 438 amino acids, 182 amino acids larger than encoded by M-CSFα and 116 amino acids smaller than encoded by M-CSFβ. M-CSFγ appears to be a result of an in-frame insertion of 546 bp (FIG. 2, #2 arrows) into M-CSFα at the same location as the 894 bp insertion forming M-CSFβ (FIG. 2, #1 arrows). Analysis of the DNA sequence (FIG. 2) shows that these 546 bp are identical to those found in M-CSFβ, indicating that the three cDNAs are probably a result of alternative splicing of M-CSF mRNA. The nucleotide sequences surrounding the insertions are similar to the consensus sequences found for mRNA donor, $C_AG/GT^A_GGT$ and acceptor, $(^TC)_nN^TCAG/G$ splice sites, as described by Mount (Nucl. Acids Res. 10:457, 1982). Splicing of the mRNA for M-CSFβ between the #1 and #2 arrows would form M-CSFα and M-CSFγ, respectively.

In its nucleic acid embodiments, the present invention provides DNA sequences comprising a single open reading frame nucleotide sequence encoding human M-CSFγ. M-CSFγ DNAs are preferably provided in a form which is capable of being expressed in a recombinant transcriptional unit under the control of mammalian, microbial, or viral transcriptional or translational control elements. For example, a sequence to be expressed in a microorganism will contain no introns. In preferred aspects, the DNA sequences comprise at least one, but optionally more than one sequence component derived from a cDNA sequence or copy thereof. Such sequences may be linked or flanked by DNA sequences prepared by assembly of synthetic oligonucleotides. However, synthetic genes assembled exclusively from oligonucleotides could be constructed using the sequence information provided herein. Exemplary sequences include those substantially identical to the nucleotide sequences depicted in FIG. 2. Alternatively, the coding sequences may include codons encoding one or more additional amino acids located at the N-terminus, for example, an N-terminal ATG codon specifying methionine linked in reading frame with the nucleotide sequence. Due to code degeneracy, there can be considerable variation in nucleotide sequences encoding the same amino acid sequence; exemplary DNA embodiments are those corresponding to the sequence of nucleotides in FIG. 2. Other embodiments include sequences capable of hybridizing to the sequence of FIG. 2 under moderately stringent conditions (50° C., 2×ssc) and other sequences degenerate to those described above which encode M-CSFγ.

Recombinant Expression of M-CSF cDNAs

Figure 3:
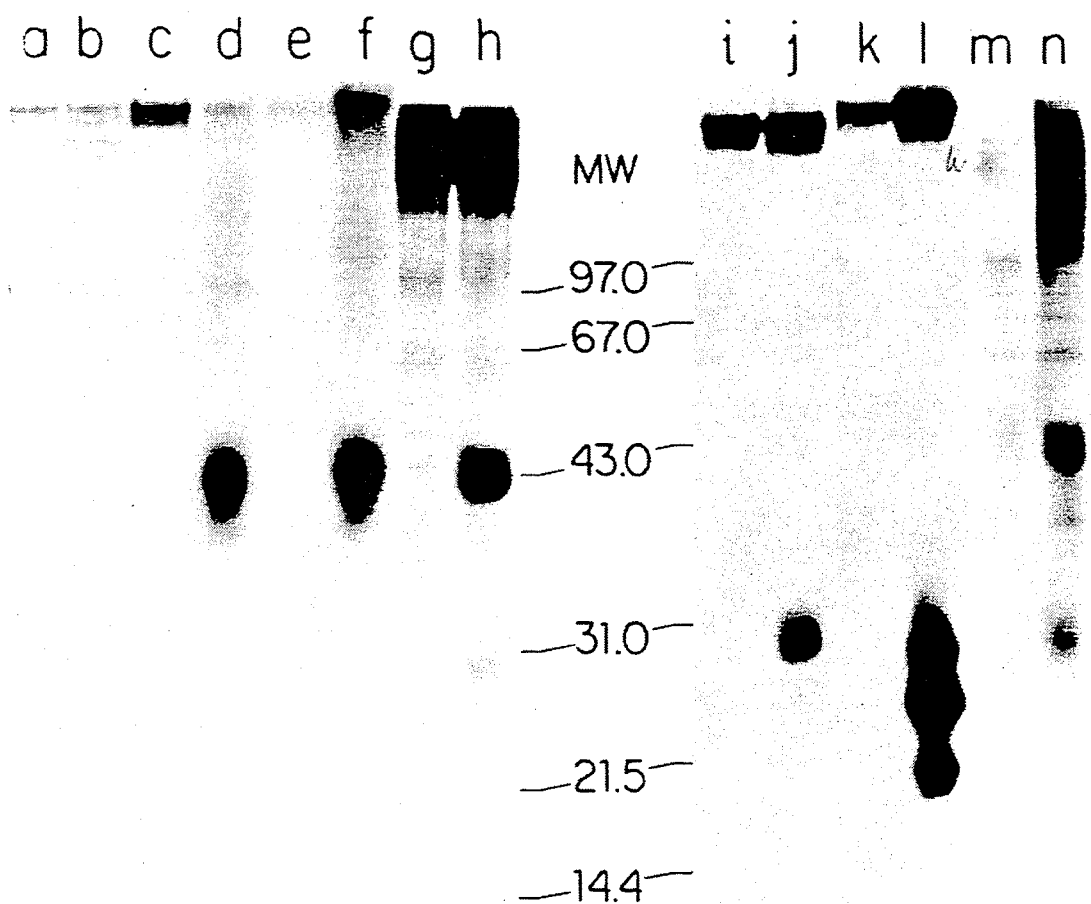
FIG. 3 is an autoradiogram of SDS-polyacrylamide gel electrophoresis of M-CSF specific proteins secreted by COS-7 cells. Supernatants from COS-7 monkey kidney cells, transfected with pDC201 (lanes a and b), pDCCSFγ (lanes c and d), pDCCSFβ (lanes e and f), pMLSV/genomic CSF-1 (lanes g and h), pDCCSFα (lanes i and j), and pDC[s]CSFα (lanes k and l), or MIA-PaCa-2 cells (lanes m and n) were collected after radiolabeling for 24 hr and immunoprecipitated with preimmune rabbit serum (lanes a, c, e, g, i, k, m) or anti-M-CSF rabbit-serum (lanes b, d, f, h, j, l, n) as described below. Immunoprecipitates were analyzed by fluorography after SDS-polyacrylamide gel (15%) electrophoresis in the presence of reducing agents. Molecular weight markers are in kilodaltons.
Figure 4:
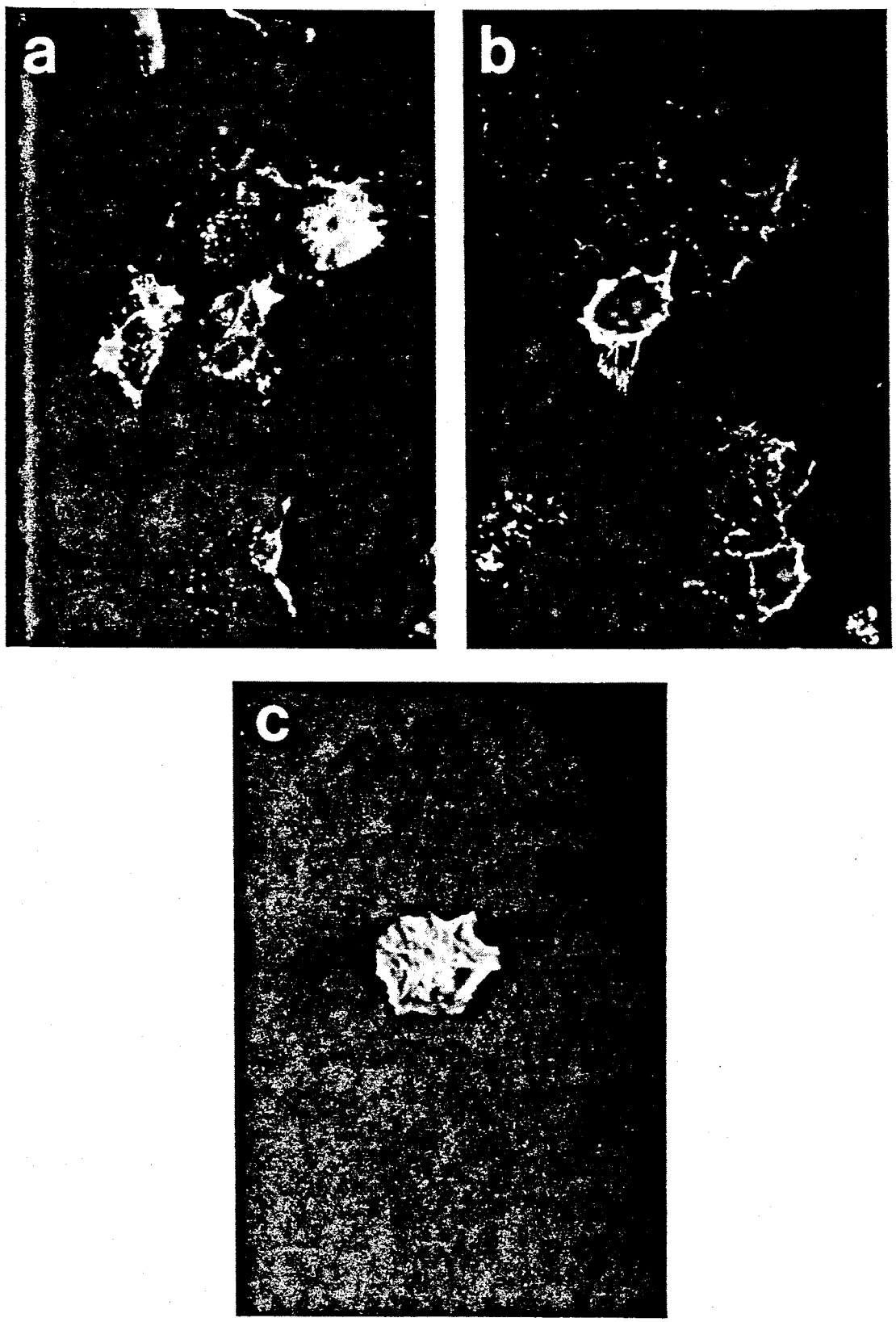
FIG. 4 is a fluorescent antibody staining of M-CSF proteins expressed on the cell surface of transfected COS-7 cells. COS-7 cells were transfected with DNA encoding M-CSFα (Panel A), M-CSFβ, (Panel B), or M-CSFγ (Panel C) and stained with rabbit antibodies directed to M-CSF followed by fluorescin isothiocyanate labeled goat anti-rabbit IgG. Each field represents a monolayer of COS-7 cells in which only those cells transfected with DNA encoding M-CSF are fluorescent. Monolayers stained with preimmune rabbit serum or transfected with DNA not encoding M-CSF or DNA encoding M-CSF in which the transmembrane region of the cDNA was deleted, did not stain with the antibody directed to M-CSF.

In order to compare the molecular weight and biological activity of the protein encoded by M-CSFγ cDNA to those encoded by M-CSFα and M-CSF cDNAs, the coding regions for M-CSFα, M-CSFβ and M-CSFγ, were inserted into the mammalian expression vector, pDC201. The resulting plasmids, designated pDCCSFα, pDCCSFβ, pDCCSFγ, were transfected into COS-7 monkey kidney cells. After 72 hr, the cultures were labeled for 24 hr with $^{35}$S-Met and $^{35}$S-Cys and M-CSF specific proteins immunoprecipitated from the supernatants with a rabbit anti-M-CSF polyclonal antiserum. Immunoprecipitates were then subjected to SDS-PAGE under reducing conditions and protein bands visualized by autoradiography. The proteins synthesized by M-CSFβ and M-CSFγ cDNAs had a molecular size of 44 kDa while M-CSFα synthesized a protein of molecular size 28 kDa (FIG. 3, lanes f, d, and j). Thus, M-CSFβ and M-CSFγ cDNAs produced proteins of similar size even though M-CSFγ cDNA encoded a precursor protein that was 116 amino acids smaller. This indicates that processing of the membrane bound precursor probably occurs upstream of Thr-363 (FIG. 2) since this residue is the last amino acid common to both cDNAs upstream of the transmembrane region. In order to prove the membrane localization of the M-CSF precursors, COS-7 cells were transfected with pDCCSFα, pDCCSFβ and pDCCSFγ and stained with the rabbit-anti-M-CSF antiserum as described in FIG. 4. In all three cases, strong surface staining of approximately 20% of the transfected cells was seen. No staining was seen with a preimmune rabbit-serum or on COS-7 cells transfected with the pDC201 vector alone.

Supernatants from the M-CSF cDNA transfections were also tested for M-CSF activity in murine and human bone marrow proliferation and colony formation assays. As can be seen from FIG. 5, all three M-CSF cDNAs produce proteins that were active on murine bone marrow cells in proliferation and monocytic colony assays. In addition they were active in the human bone marrow monocytic colony assay although at a much lower level than in the mouse assay. Surprisingly, no activity was detected in the human bone marrow proliferation assay.

Several observations can be made from analysis of the proteins released by COS-7 cells transfected with the genomic clone of M-CSF, M-CSFα, M-CSFβ, M-CSFγ cDNAs, and a mutated form of M-CSFα, [s]M-CSFα, that lacks the membrane-spanning region. First, the two predominant proteins produced by M-CSFα, M-CSFβ and M-CSFγ (44 kDa and 28 kDa) are also produced by the genomic M-CSF clone indicating that the three cDNA species are probably not artifactual. The same two M-CSF proteins are found in supernatants of MIA-PaCa-2 cells, a source of non-recombinant human M-CSF. Secondly, the cleavage site for the proteins synthesized by M-CSFβ and M-CSFγ must be upstream of Thr-363 as they both synthesize a protein of similar size (44 kDa). The amino acids that are present in M-CSFβ but not in M-CSFγ are therefore not required for processing of the protein. This region includes two potential N-linked glycosylation sites (FIG. 2). Third, the transmembrane region which may be involved in the normal processing of M-CSF, is not required to synthesize a biologically active secreted protein. This was illustrated by construction of a mutant form of M-CSF, [s]M-CSFα, which lacks the transmembrane region. This cDNA encodes a secreted protein indistinguishable in its activity from those produced by M-CSFα, M-CSFβ and M-CSFγ. Fourth, a large portion of the coding region in M-CSFα, M-CSFβ and M-CSFγ, is not required for biological activity (as defined by in vitro bone marrow assays) in that a protein with only 159 amino acids (encoded by [s]CSFM-CSFα, M-CSFβ and M-CSFα) is fully active. In fact cDNA encoding for as few as 147 amino acids (amino acids 33 to 179, FIG. 2) has been constructed. When transformed into yeast cells this cDNA yields an M-CSF protein with full biological activity.

The three membrane bound precursors may present different proteolytic cleavage sites that are cleaved by different proteases, located at different sites in the body, releasing secreted M-CSF. Alternatively, the membrane-bound M-CSF molecules could function as cell-surface ligands. While no conclusive evidence is presently available, the membrane bound M-CSF may be biologically active, requiring direct cell-to-cell contact for binding to M-CSF receptors on adjacent cells to initiate a biological response. The three different M-CSF cDNAs would extend the receptor-binding site of M-CSF (within the amino-terminal 147 amino acids) various distances from the cell membrane.

All of the reported cDNA sequences for M-CSF result in the production of biologically active M-CSF proteins by COS-7 cells. The data in FIG. 5 also confirm that the recombinant human M-CSFγ has much less biological activity on human bone marrow cells than they have on comparable populations of murine bone marrow cells. In colony assays, human M-CSF appears to be 50-200 fold more active on murine bone marrow then on human bone marrow. In addition, while human M-CSF(s) will cause murine bone marrow cells to proliferate, they have no mitogenic effect on bone marrow cells of human origin, contrary to their previously reported role in bone marrow development. In contrast to M-CSF, human GM-CSF (FIG. 5) stimulates colony formation and exhibits potent mitogenic activity on human bone marrow. The inability of M-CSF to stimulate significant proliferation of human bone marrow cells can also be seen by direct analysis of the colonies formed in soft agar. In contrast to the large size of the colonies stimulated in murine bone marrow by human M-CSF(s) or the large size of colonies produced in response to GM-CSF stimulation of human marrow (>50-2000 cells), the colonies generated by M-CSF stimulation of human marrow contain far fewer cells ($\leq 50$ cells). These data raise the question of the role of M-CSF in human hematopoiesis. In the murine system it is clear that M-CSF is a potent colony stimulating factor which is required for survival, growth, and differentiation of the mononuclear macrophage lineage. It is possible that in humans, M-CSF has lost many of these functions and its main role is as an effector of mature macrophages. Alternatively, perhaps its main role is not that of a soluble cytokine but that of a cell membrane family of molecules, the expression of which may direct cell to cell interactions important to the regulation of hematopoiesis.

The present invention also provides expression vectors for producing useful quantities of purified M-CSFγ. The vectors can comprise synthetic or cDNA-derived DNA fragments encoding human M-CSFγ or bioequivalent homologues operably linked to regulatory elements derived from mammalian, bacterial, yeast, bacteriophage, or viral genes. Useful regulatory elements are described in greater detail below. Following transformation, transfection or infection of appropriate cell lines, such vectors can be induced to express recombinant protein.

Human M-CSFγ can be expressed in mammalian cells, yeast, bacteria, or other cells under the control of appropriate promoters. Cell-free translation systems could also be employed to produce human M-CSFγ using RNAs derived from the DNA constructs of the present invention. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference.

Various mammalian cell culture systems can be employed to express recombinant protein. Examples of suitable mammalian host cell lines include the COS-7 lines of monkey kidney cells, described by Gluzman (Cell 23:175, 1981), and other cell lines capable of expressing an appropriate vector, for example, the C127, 3T3, CHO, HeLa and BHK cell lines. Mammalian expression vectors may comprise nontranscribed elements such as an origin of replication, a suitable promoter and enhancer, and other 5' or 3' flanking nontranscribed sequences, and 5' or 3' nontranslated sequences, such as necessary ribosome binding sites, a polyadenylation site, splice donor and acceptor sites, and termination sequences. DNA sequences derived from the SV40 viral genome, for example, SV40 origin, early promoter, enhancer, splice, and polyadenylation sites may be used to provide the other genetic elements required for expression of a heterologous DNA sequence. Additional details regarding the use of mammalian high expression vector to produce recombinant human M-CSFγ are provided in Examples 2 and 3 below. Exemplary vectors can be constructed as disclosed by Okayama and Berg (Mol. Cell. Biol. 3:280, 1983).

A useful system for stable high level expression of M-CSFγ cDNAs in C127 murine mammary epithelial cells can be constructed substantially as described by Cosman et al. (Mol. Immunol. 23:935, 1986).

Yeast systems, preferably employing Saccharomyces species such as S. cerevisiae, can also be employed for expression of the recombinant proteins of this invention. Yeast of other genera, for example, Pichia or Kluyveromyces, have also been employed as production strains for recombinant proteins.

Generally, useful yeast vectors will include origins of replication and selectable markers permitting transformation of both yeast and E. coli, e.g., the ampicillin resistance gene of E. coli and S. cerevisiae TRP1 gene, and a promoter derived from a highly expressed yeast gene to induce transcription of a downstream structural sequence. Such promoters can be derived from yeast transcriptional units encoding highly expressed genes such as 3-phosphoglycerate kinase (PGK), α-factor, acid phosphatase, or heat shock proteins, among others. The heterologous structural sequence is assembled in appropriate reading frame with translation initiation and termination sequences, and, preferably, a leader sequence capable of directing secretion of translated protein into the extracellular medium. Optionally, the heterologous sequence can encode a fusion protein including an N-terminal identification peptide (e.g., Asp-Tyr-Lys-(Asp)$_4$-Lys) or other sequence imparting desired characteristics, e.g., stabilization or simplified purification of expressed recombinant product.

Useful yeast vectors can be assembled using DNA sequences from pBR322 for selection and replication in E. coli (Amp$^r$ gene and origin of replication) and yeast DNA sequences including a glucose-repressible alcohol dehydrogenase 2 (ADH2) promoter. The ADH2 promoter has been described by Russell et al. (J. Biol. Chem. 258:2674, 1982) and Beier et al. (Nature 300:724, 1982). Such vectors may also include a yeast TRP1 gene as a selectable marker and the yeast 2μ origin of replication. A yeast leader sequence, for example, the α-factor leader which directs secretion of heterologous proteins from a yeast host, can be inserted between the promoter and the structural gene to be expressed (see Kurjan et al., U.S. Pat. No. 4,546,082; Kurjan et al., Cell 30:933 (1982); and Bitter et al., Proc. Natl, Acad. Sci. USA 81:5330, 1984). The leader sequence may be modified to contain, near its 3' end, one or more useful restriction sites to facilitate fusion of the leader sequence to foreign genes.

Suitable yeast transformation protocols are known to those skilled in the art; an exemplary technique is described by Hinnen et al. (Proc. Natl. Acad. Sci. USA 75:1929, 1978), selecting for Trp+ transformants in a selective medium consisting of 0.67% yeast nitrogen base, 0.5% casamino acids, 2% glucose, 10 μg/ml adenine and 20 μg/ml uracil.

Host strains transformed by vectors comprising the ADH2 promoter may be grown for expression in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Useful expression vectors for bacterial use are constructed by inserting a DNA sequence encoding human M-CSFγ together with suitable translation initiation and termination signals in operable reading phase with a functional promoter. The vector will comprise one or more phenotypic selectable markers and an origin of replication to ensure amplification within the host. Suitable prokaryotic hosts for transformation include E. coli, Bacillus subtilis, Salmonella typhimuium, and various species within the genera Pseudomonas, Streptomyces, and Staphylococcus, although others may also be employed as a matter of choice.

Expression vectors are conveniently constructed by cleavage of cDNA clones at sites close to the codon encoding the N-terminal residue of the mature protein. Synthetic oligonucleotides can then be used to "add back" any deleted sections of the coding region and to provide a linking sequence for ligation of the coding fragment in appropriate reading frame in the expression vector, and optionally a codon specifying an initiator methionine.

As a representative but nonlimiting example, useful expression vectors for bacterial use can comprise a selectable marker and bacterial origin of replication derived from commercially available plasmids comprising genetic elements of the well-known cloning vector pBR322 (ATCC 37017). Such commercial vectors include, for example pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

A particularly useful bacterial expression system employs the phage λP$_L$ promoter and cI857 thermolabile repressor. Plasmid vectors available from the American Type Culture Collection which incorporate derivative of the λP$_L$ promoter include plasmid pHUB2, resident in E. coli strain JMB9 (ATCC 37092) and pPLc28, resident in E. coli RR1 (ATCC 53082). Other useful promoters for expression in E. coli include the T7 RNA polymerase promoter described by Studier et al. (J. Mol. Biol. 189:113, 1986), the lacZ promoter described by Lauer (J. Mol. Appl. Genet. 1:139–147, 1981) and available as ATCC 37121, and the tac promoter described by Maniatis (Molecular Cloning: A Laboratory Manual, Cold Spring Harbor Laboratory, 1982, p 412) and available as ATCC 37138.

Following transformation of a suitable host strain and growth of the host strain to an appropriate cell density, the selected promoter is derepressed by appropriate means (e.g., temperature shift or chemical induction) and cells cultured for an additional period. Cells are typically harvested by centrifugation, disrupted by physical or chemical means, and the resulting crude extract retained for further purification. Cells are grown, for example, in a 10 liter fermenter employing conditions of maximum aeration and vigorous agitation. An antifoaming agent (Antifoam A) is preferably employed. Cultures are grown at 30° C. in the superinduction medium disclosed by Mott et al. (Proc. Natl. Acad. Sci. USA 82:88, 1985), alternatively including antibiotics, derepressed at a cell density corresponding to $A_{600}=0.4-0.5$ by elevating the temperature to 42° C., and harvested from 2-20 hours, preferably 3-6 hours, after the upward temperature shift. The cell mass is initially concentrated by filtration or other means, then centrifuged at 10,000×g for 10 minutes at 4° C. followed by rapidly freezing the cell pellet.

Preferably, purified human M-CSFγ or bioequivalent homologues are prepared by culturing suitable host/vector systems to express the recombinant translation products of the synthetic genes of the present invention, which are then purified from culture media.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant mammalian M-CSFγ can be disrupted by any convenient method, including freeze-thaw cycling, sonication, mechanical disruption, or use of cell lysing agents.

Fermentation of yeast which express mammalian M-CSFγ as a secreted protein greatly simplifies purification. Secreted recombinant protein resulting from a large-scale fermentation can be purified by methods analogous to those disclosed by Urdal et al. (J. Chromatog. 296:171, 1984). This reference describes two sequential, reversed-phase HPLC steps for purification of recombinant human GM-CSF on a preparative HPLC column.

In its various embodiments, the present invention provides substantially homogeneous recombinant human M-CSFγ polypeptides free of contaminating endogenous materials, with or without associated native-pattern glycosylation. The native human M-CSF molecule is recovered from cell culture extracts as a glycoprotein having an apparent molecular weight of about 45 kDa. M-CSFγ expressed in mammalian expression systems, e.g., COS-7 cells, has a theoretical molecular weight of 47,890 including the leader sequence.

Recombinant M-CSFγ proteins within the scope of the present invention also include N-terminal methionyl human M-CSFγ. Additional embodiments include soluble truncated versions wherein certain regions, for example, the transmembrane region with associated terminal portions, and intracellular domains, are deleted. Also contemplated are human M-CSFγ expressed as fusion proteins with a polypeptide leader comprising the sequence Asp-Tyr-Lys-(Asp$_4$)-Lys, or with other suitable peptide or protein sequences employed as aids to expression in microorganisms or purification of microbially-expressed proteins.

Bioequivalent homologues of the proteins of this invention include various analogs, for example, truncated versions of M-CSFγ wherein internal residues or sequences not needed for biological activity are deleted. Other analogs contemplated herein are those in which one or more cysteine residues have been deleted or replaced with other amino acids, for example, neutral amino acids. Other approaches to mutagenesis involve modification of adjacent dibasic amino acid residues to enhance expression in yeast systems in which KEX2 protease activity is present, or modification of the protein sequence to eliminate one or more N-linked glycosylation sites.

As used herein, "mutant amino acid sequence" refers to a polypeptide encoded by a nucleotide sequence intentionally made variant from a native sequence. "Mutant protein" or "analog" means a protein comprising a mutant amino acid sequence. "Native sequence" refers to an amino acid or nucleic acid sequence which is identical to a wild-type or native form of a gene or protein. The terms "KEX2 protease recognition site" and "N-glycosylation site" are defined below. The term "inactivate," as used in defining particular aspects of the present invention, means to alter a selected KEX2 protease recognition site to retard or prevent cleavage by the KEX2 protease of *S. cerevisiae*, or to alter an N-glycosylation site to preclude covalent bonding of oligosaccharide moieties to particular amino acid residues by the cell.

Site-specific mutagenesis procedures can be employed to inactivate KEX2 protease processing sites by deleting, adding, or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites. The resulting analogs are less susceptible to cleavage by the KEX2 protease at locations other than the yeast α-factor leader sequence, where cleavage upon secretion is intended.

Many secreted proteins acquire covalently attached carbohydrate units following translation, frequently in the form of oligosaccharide units linked to asparagine side chains by N-glycosidic bonds. Both the structure and number of oligosaccharide units attached to a particular secreted protein can be highly variable, resulting in a wide range of apparent molecular masses attributable to a single glycoprotein. Attempts to express glycoproteins in recombinant systems can be complicated by the heterogeneity attributable to this variable carbohydrate component. For example, purified mixtures of recombinant glycoproteins such as human or murine granulocyte-macrophage colony stimulating factor (GM-CSF) can consist of from 0 to 50% carbohydrate by weight. Miyajima et al. (EMBO J. 5:1193, 1986) reported expression of a recombinant murine GM-CSF in which N-glycosylation sites had been mutated to preclude glycosylation and reduce heterogeneity of the yeast-expressed product.

The presence of variable quantities of associated carbohydrate in recombinant glycoproteins complicates purification procedures, thereby reducing yield. In addition, should the glycoprotein be employed as a therapeutic agent, a possibility exists that recipients will develop immune reactions to the yeast carbohydrate moieties, requiring therapy to be discontinued. For these reasons, biologically active, homogeneous analogs of immuno-regulatory glycoproteins having reduced carbohydrate may be desirable for therapeutic use.

Functional mutant analogs of human M-CSFγ having inactivated N-glycosylation sites can be produced by oligonucleotide synthesis and ligation or by site-specific mutagenesis techniques as described below. These analog proteins can be produced in a homogeneous, reduced-carbohydrate form in good yield using yeast expression systems. N-glycosylation sites in eukaryotic proteins are characterized by the amino acid triplet Asn-$A^1$-Z, where $A^1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A^1$ and Z, or an amino acid other than Asn between Asn and $A^1$. Preferably, substitutions are made conservatively; i.e., the most preferred substitute amino acids are those having physicochemical characteristics resembling those of the residue to be replaced. Similarly, when a deletion or insertion strategy is adopted, the potential effect of the deletion or insertion upon biological activity should be considered.

In addition to the particular analogs described above, numerous DNA constructions including all or part of the nucleotide sequences depicted in FIG. 2, in conjunction with oligonucleotide cassettes comprising additional useful restriction sites, can be prepared as a matter of convenience. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. By way of example, Walder et al. (Gene 42:133, 1986); Bauer et al. (Gene 37:73, 1985); Craik (Biotechniques, January 1985, 12-19); Smith et al. (Genetic Engineering: Principles and Methods, Plenum Press, 1981); and U.S. Pat. No. 4,518,584 disclose suitable techniques, and are incorporated by reference herein.

Mutational Analysis of M-CSF

As mentioned above, soluble M-CSF is processed from a membrane-bound precursor. To test whether the transmembrane region is required for synthesis of an active M-CSF protein, a mutant M-CSFα gene, [s]M-CSFα, that lacks the carboxyl-terminal 66 amino acids of M-CSFα including the transmembrane region was constructed. The mutant M-CSF gene was inserted into pDC201 resulting in pDC[s]CSFα. The plasmid was transfected into COS-7 cells and supernatants were collected and analyzed as before. Fluorescent staining of COS-7 cells containing this construct failed to detect membrane bound forms of M-CSF. However, SDS-PAGE shows that [s]M-CSFα yields proteins of 18 kDa, 22 kDa and 28 kDa (FIG. 3, lane l) that are present in the supernatant. Two of the three protein bands are likely a result of glycosylation at one or two of the potential N-linked glycosylation sites (Asn-154 and Asn-182, FIG. 2). The protein band at 18 kDa agrees well with the predicted size of nonglycosylated [s]M-CSFα (18.5 kDa). The fully glycosylated form of [s]M-CSFα (28 kDa) is similar in size to the protein synthesized by M-CSFα (FIG. 3, lane j). These results support the theory that the transmembrane region present in the precursor protein encoded by M-CSFα may indeed be absent from the secreted product. The proteins synthesized by [s]M-CSFα were also active in the murine bone marrow assay and human bone marrow colony assay but not the human bone marrow proliferation assay (FIG. 5). These results indicate that the transmembrane region of M-CSFα, which may be involved in the normal processing of M-CSF, is not required for secretion of a biologically active protein.

Isolation and Expression of a Genomic M-CSF Clone

Transcription of the gene for human M-CSF results in several mRNA species encoding at least three different M-CSF precursor proteins. When expressed in COS-7 cells, glycosylated subunit proteins of 44 kDa or 28 kDa are released. In order to determine if additional M-CSF related proteins exist, a genomic clone of M-CSF was isolated and expressed in COS-7 cells. A human genomic λ-phage library (Lawn et al., Cell 15:1157, 1978) was screened with the [s]M-CSFα probe resulting in the isolation of two distinct classes of clones, λCSF-1-1 and λCSF-1-12, with inserts of 11.9 kbp and 13.0 kbp respectively. Restriction mapping and Southern hybridization analysis using synthetic oligonucleotide probes specific for the 5'- and 3'-non-coding regions of M-CSF indicated that the two λ clones overlapped and contained all of the coding exons of the M-CSF gene (FIG. 1B). Together, the λ-phage clones defined 17.3 kbp of the M-CSF gene. They appeared however to lack the majority of the 3'-non-coding exons. Using the common XhoI site, DNA fragments from λCSF-1-1 and λCSF-1-12 that contained the coding exons of the M-CSF gene were inserted into the mammalian cell expression vector, pMLSV (Cosman et al., Nature 312:768, 1984), resulting in the plasmid, pMLSV/genomic-CSF-1. After transfection into COS-7 cells, supernatants were analyzed as described above. As can be seen from the autoradiogram in FIG. 3 lane h, the genomic clone of M-CSF produced two forms of M-CSF with molecular sizes of 44 kDa and 28 kDa that were identical in size to the proteins encoded by M-CSFα, M-CSFβ and M-CSFγ cDNAs, although at lower levels (longer exposure time). Supernatants from the genomic M-CSF transfection were also found to be active in the murine and human bone marrow colony assays and the murine bone marrow proliferation assay, although at reduced levels (FIG. 5). The lower protein production probably reflects decreased plasmid replication in the COS-7 cells due to the large size of the pMLSV/genomic-CSF-1 plasmid (23.5 kbp). As before, no activity was detected in the human bone marrow proliferation assay. These results indicate that the predominant forms of M-CSF are proteins of 44 kDa and 28 kDa.

These results were further substantiated by analysis of mitogen stimulated MIA-PaCa-2 cells. MIA-PaCa-2 is a human pancreatic tumor cell line known to synthesize M-CSF. Mia-PaCa-2 cells were labeled for 24 hr with $^{35}$S-Met and $^{35}$S-Cys, supernatants collected and M-CSF specific proteins immunoprecipitated. SDS-PAGE analysis revealed two predominant protein bands of 44 kDa and 28 kDa (FIG. 3, lane n). These proteins were the same size as those synthesized by M-CSFα, M-CSFβ, M-CSFγ and the genomic clone of M-CSF.

The following examples are offered by way of illustration, and not by way of limitation.

Example 1: Isolation of M-CSF cDNA and Genomic Clones

For mRNA isolation, human pancreatic tumor cells, Mia-PaCa-2 (ATCC #CRL1420) (Wu et al., J. Biol. Chem. 254:6226, 1979), were grown in RPMI 1640 with 0.292 mg/ml glutamine, 0.2 g/l penicillin, and 0.2 g/l stretomycin and 10% fetal calf serum to one day preconfluence and then stimulated for two days with phorbol myristate acetate (PMA, 50 ng/ml). Procedures for mRNA purification and cDNA synthesis have been described by Cosman et al., Nature 312:768, 1984, and March et al., Nature 315:641, 1985, and are incorporated herein by reference. The cDNA was modified with EcoRI linkers, cloned into $\lambda$gt10, packaged in vitro, and used to infect E. coli strain C600 hfl$^-$ according to the procedure described by Huynh et al. (DNA Cloning: A Practical Approach, IRL Press, Oxford, 1985) ($\lambda$gt10, packaging kits and bacterial hosts purchased from Stratagene). Independent plaques ($5 \times 10^5$) were blotted onto nitrocellulose filters (Schleicher and Schuell, Keene, N.H.), and hybridized with a $^{32}$P-labeled human M-CSF probe. The probe was $^{32}$P-labeled by nick-translating a 420 bp PstI/XbaI DNA fragment of [s]M-CSFα which consists of nucleotides 141 to 544 and 1439 to 1467 (FIG. 2). The [s]M-CSFα gene was assembled from 16 synthetic oligonucleotides and contains the first 158 amino acids of M-CSFα. Filters were incubated 24 hr at 37° C. with $5 \times 10^5$ cpm/ml probe in Stark's hybridization buffer (see Wahl et al., Proc. Natl. Acad. Sci. USA 76:3683, 1979) consisting of 50% formamide, 5×SSC (0.75M NaCl/0.075M trisodium citrate pH 7), 50 mM KH2PO4 pH 6.5, ficoll, polyvinylpyrrolidone, and bovine serum albumin at 0.04% each, 0.1% sodium dodecyl sulfate (SDS), 20 mM EDTA, and 150 μg/ml salmon sperm DNA. Filters were then washed extensively in 6×SSC at room temperature followed by successive washes at 55° C. in 6×SSC, 2×SSC/0.1% SDS, and finally 0.5×SSC/0.1% SDS, prior to autoradiography. After rescreening positive plaques, cDNA inserts were isolated and sub-cloned into pGEMBL18 for DNA sequencing according to the techniques of Hattori and Sakaki (Anal. Biochem. 152:272, 1986) and Sanger et al. (Proc. Natl. Acad. Sci. USA 74:3463, 1977). Plasmid pGEMBL18 is a derivative of pGEMBL18 (see Dente et al., Nucl. Acids Res. 11:1645, 1983), in which the promoters for Sp6 and T7 polymerases flank the multiple cloning site. Sequence analysis was done by programs designed by the University of Wisconsin Genetics Computer Group described by Devereux et al. (Nucl. Acids Res. 12:387, 1984).

A human $\lambda$-phage genomic library ($1 \times 10^6$ plaques) described by Lawn et al. (Cell 15:1157, 1978), was screened with a $^{32}$P-labeled M-CSF probe as described above except that hybridizations were conducted at 55° C. in 6×SSC and washes were performed at 68° C. in 1×SSC. DNA from positive plaques was isolated and characterized by restriction mapping and Southern blot analysis as described by Maniatis et al. (Molecular Cloning: A Laboratory Manual, Cold Spring Harbor Laboratory Press, New York, 1982) using $^{32}$P-labeled oligonucleotide probes complementary to the 5' non-coding and 3' non-coding regions (nucleotides 106-124 and 968-987, respectively) of M-CSFα. The oligonucleotides were $^{32}$P-labeled with T4 polynucleotide kinase.

Example 2: Construction of M-CSF Expression Plasmids

Plasmids, designed to synthesize and secrete M-CSF, were constructed by inserting DNA fragments encoding M-CSFα, M-CSFβ, M-CSFγ and the genomic sequences of M-CSF into the mammalian expression plasmids, pDC201 or pMLSV. Plasmid pDC201 is a derivative of pMLSV. pDCCSFβ was constructed by blunt-ending the 1720 bp EcoRI fragment (from the λ phage cDNA isolate, λ-13) containing the entire coding region of M-CSFβ and inserting it into the SmaI site of pDC201. As the cDNA isolate of M-CSFγ (λ-8) lacked the first 140 amino acids, we constructed a hybrid between M-CSFβ and M-CSFγ by substituting DNA sequence downstream of the NcoI site in M-CSFβ with sequence downstream of the NcoI site from M-CSFγ (FIG. 1A). This was accomplished by ligating together: a 1500 bp SfiI/NcoI fragment from pDCCSFβ (SfiI site is from pDC201 and is upstream of the M-CSFβ coding region) containing amino acids 1–214, a 650 bp NcoI/EcoRI (blunted) fragment from λ-8 containing the carboxyl 224 amino acids of M-CSFγ and a 4500 bp SfiI/SmaI fragment from pDC201, resulting in plasmid pDCCSFγ. For construction of an expression vector containing M-CSFα, we used a synthetic version of M-CSFα which was constructed from twenty oligonucleotides. This was accomplished by ligating the 670 bp BstXI/XbaI fragment containing the distal 214 amino acids of mature M-CSFα to the signal sequence of the interleukin-2 receptor contained in a SstI/XbaI fragment of pN1/N4-S with the aid of oligonucleotides encoding the first 10 amino acids of mature M-CSFα. The coding region of M-CSFα together with the signal sequence of the interleukin-2 receptor was then excised by XbaI digestion, blunt-ended, and ligated to the SmaI site of pDC201 resulting in plasmid pDCCSFα. In a similar manner the truncated version of M-CSFα, [s]M-CSFα, was inserted into pDC201 resulting in plasmid pDC[s]CSFα.

The genomic expression vector pMLSV/genomic-CSF-1 was constructed as follows. A fragment encoding the 3' portion of the CSF-1 gene from the XhoI site to a ClaI site in the λ arm (from λCSF-1-12) was subcloned into a plasmid having a polylinker containing XhoI, AccI and NotI sites. Insertion between the XhoI and AccI sites allowed the CSF-1-12 3' end fragment to be re-isolated as a XhoI-NotI fragment. This was ligated together with a SpeI/XhoI fragment from λCSF-1-1 into the mammalian expression plasmid, pMLSV, that had been cut with XbaI and NotI. The XbaI and NotI sites are present in a polylinker in between the SV40 early promoter and the SV40 splicing/polyadenylation signals.

Example 3: Transfection of COS-7 cells and analysis of M-CSF

COS-7 cells (10 cm plates) were transfected by a standard DEAE-dextran method, such as that described previously by Cosman et al. (Nature 312:768, 1984) with the pDCCSFγ vector DNA three days prior to collection of media for M-CSF assays or labeling. For labeling, each plate of cells was washed twice with phosphate buffered saline and incubated in 3 ml of MEM without methionine and cysteine. After the addition of $^{35}$S-methionine and $^{35}$S-cysteine (100 μCi "Translabel", Amersham) the cells were incubated for 24 hours at 37° C. The media, containing secreted M-CSF species, was removed and centrifuged for 5 min in a microfuge. Proteinase inhibitors were added to the supernatants at final concentrations of 5 mM EDTA, 5 mM EGTA, 10 μg/ml soybean trypsin inhibitor, 10 μM leupeptin, 10 μM pepstatin A, 10 μM o-phenanthroline, and 25 mM benzamidine-HCl. A preclearing reaction was performed by addition of 5 μl of preimmune rabbit serum and 50 μl of a 20% suspension of protein A Sepharose. After incubation at 4° C. on a rocker for 30 min., the suspension was centrifuged in a microfuge for 5 min. The supernatants were incubated with 5 μl of preimmune serum or 5 μl of anti-M-CSF rabbit serum and 70 μl of a 20% suspension of protein A Sepharose for 4 hours at 4° C. The immunoprecipitates were then washed four times in RIPA buffer (50 mM HEPES, pH 8.0, 150 mM NaCl, 0.5% sodium deoxycholate, 0.5% nonidet P-40, and 0.1% SDS), and boiled in SDS sample buffer containing 1 mM dithiothreitol. Following centrifugation, the supernatants were removed and stored at −20° C. until electrophoresis on a 15% SDS-polyacrylamide gel.

MIA-PaCa-2 cells were labeled as above and the resulting media, containing radiolabeled M-CSF, was harvested and processed identically to supernatants from transfected COS-7 cells.

Example 4: Preparation of Anti-M-CSF Rabbit Serum

Adult female New Zealand rabbits were obtained from R and R Rabbitry (Sultan, Wash.). All immunizations were given intradermally. Rabbits initially received 100 μg of purified yeast generated recombinant [s]M-CSFα emulsified 1:1 in complete Freund's adjuvant. In all subsequent immunizations the antigen was emulsified 1:1 in incomplete Freund's adjuvant. The rabbits received 100 μg on day 22, 250 μg on days 41 and 58, and 200 μg on days 79, 156, and 192. Bleeds were taken 10 days after every injection and the serum titers to [s]M-CSFα determined by dot blot analysis as described by Conlon et al. (J. Immunol. 135:328, 1985). A final bleed was obtained on day 205. At a 1:130,000 dilution, this serum could detect 25 ng of [s]M-CSFα by immunodot-blot.

Example 5: Fluorescent Staining of Transfected COS-7 Cells

COS-7 cells were transfected as described above and cultured on glass slides (1×3 in, Lab-Tek, Naperville, Ill.) for 72 hr. Rabbit antisera, directed to M-CSF, was diluted 1:1000 in RPMI 1640 containing 2% bovine serum albumin, 20 mM Hepes, and 0.2% sodium azide, added to the cell monolayers for 60 min at 4° C., and washed three times with cold RPMI 1640. Goat anti-rabbit IgG, to which fluorescin isothiocyanate had been coupled (TAGO, Burlingame, Calif.) was then diluted 1:50 and added to the cell monolayers. After 30 min., monolayers were washed with RPMI 1640 and examined on a Leitz Dialux 20EB fluorescence microscope. Photographs were taken using an Olympus photomicrographic system model PM-10AD with Kodak Ektrachrome P800/1000 film. Controls included the use of preimmune rabbit serum as well as monolayers of COS-7 cells transfected with non-M-CSF containing DNA.

Example 6: Bone Marrow Assays

Procedures for preparation of human bone marrow and human bone marrow colony assays have been described by Cantrell et al. (Proc. Natl. Acad. Sci. USA 82:6250, 1985). For the human bone marrow proliferation assay, serial threefold dilutions of sample were made in 96-well tissue culture-treated microtiter plates, so that the final volume in each well was 50 μl. Thereafter, 50 μl of the bone marrow cell suspension ($2.5 \times 10^5$ cells/mL) was added to each well. Plates were incubated for 96 hr. at which time 25 μl of medium containing 80 μCi/ml 3H-thymidine (3H-Tdr, 80 Ci/mM, New England Nuclear NET-027Z) was added to each well and incubation continued for an additional 5 hr. The contents of each well were harvested into glass fiber strips using a multiple automated sample harvester and radionuclide incorporation was assessed by liquid scintillation counting. Units of activity were determined as the inverse of the dilution which yielded 50% of maximal level of 3H-Tdr incorporated in response to stimulation with a known standard (purified recombinant human GM-CSF).

Murine bone marrow colony assays were performed with COS-7 cell supernatants in a traditional semi-solid agar assay using $10^5$ bone marrow cells per ml (see Stanley, Meth. Enzymol., Academic Press, New York, 1985). The CFU-C per ml was defined as the reciprocal of the dilution multiplied by the number of colonies observed at one half the maximal response. Colonies were all of macrophage lineage. For the murine bone marrow proliferation assay, bone marrow derived macrophages (BMM) were obtained as described by Tushinski et al. (Cell 28:71, 1982). Briefly, $C_3H/Hej$ bone marrow cells ($1 \times 10^6$/ml) were seeded into tissue culture flasks (Falcon) at a density of $2.9 \times 10^5$ cells/cm$^2$ in the presence of 1000 units/ml of partially purified M-CSF from L929 fibroblast conditioned medium. The culture media consisted of alpha MEM (Gibco) supplemented with 15% fetal calf serum, 0.292 mg/ml glutamine, 0.02 mg/ml asparagine, $5 \times 10^{-5}$M 2-mercaptoethanol, 0.2 g/l penicillin and 0.2 g/l streptomycin. After three days the nonadherent cells were harvested and used in a proliferation assay. COS-7 cell supernatants were serially diluted into 96 well microtiter plates. Then BMM, at $2 \times 10^5$/ml, were added to the samples in a final volume of 100 μl.

Following a five hour incubation at 37° C. in 10% CO$_2$, the cultures were pulsed with 2 μCi 3H-Tdr. After a total incubation time of 24 hours, the cultures were harvested onto glass fiber filters and 3H-Tdr measured by liquid scintillation counting. One unit of activity was defined as the amount of sample necessary to induce 50% of maximal 3H-Tdr incorporated as compared to a known standard (conditioned media from murine L929 cell).

Example 7: Expression of M-CSFγ in Yeast

For expression of human or murine M-CSFγ in yeast, a yeast expression vector derived from pIXY120 is constructed as follows. pIXY120 is identical to pYα-HuGM (ATCC 53157), except that it contains no cDNA insert and includes a polylinker/multiple cloning site with an NcoI site. This vector includes DNA sequences from the following sources: (1) a large SphI (nucleotide 562) to EcoRI (nucleotide 4361) fragment excised from plasmid pBR322 (ATCC 37017), including the origin of replication and the ampicillin resistance marker for selection in E. coli; (2) S. cerevisiae DNA including the TRP-1 marker, 2μ origin of replication, ADH2 promoter; and (3) DNA encoding an 85 amino acid signal peptide derived from the gene encoding the secreted peptide α-factor (See Kurjan et al., U.S. Pat.

No. 4,546,082). An Asp718 restriction site was introduced at position 237 in the α-factor signal peptide to facilitate fusion to heterologous genes. This was achieved by changing the thymidine residue at nucleotide 241 to a cytosine residue by oligonucleotide-directed in vitro mutagenesis as described by Craik, Biotechniques: 12 (1985). A synthetic oligonucleotide containing multiple cloning sites and having the following sequence was inserted from the Asp718 site at amino acid 79 near the 3' end of the α-factor signal peptide to a SpeI site in the 2μ sequence:

```
Asp718                                          StuI    NcoI    BamHI
GTACCTTTGGATAAAAGAGACTACAAGGACGACGATGACAAGAGGCCTCCATGGAT...
    GAAACCTATTTTCTCTGATGTTCCTGCTGCTACTGTTCTCCGGAGGTACCTA...
                                        |←——— Polylinker ———

SmaI          SpeI
                                 ...CCCCCGGGACA
                                 ...GGGGGCCCTGTGATC
                                 ———— Polylinker ————→|
``` pBC120 also varies from pYαHuGM by the presence of a 514 bp DNA fragment derived from the single-standed phage f1 containing the origin of replication and intergenic region, which has been inserted at the NruI site in the pBR322 sequence. The presence of an f1 origin of replication permits generation of single-stranded DNA copies of the vector when transformed into appropriate strains of *E. coli* and superinfected with bacteriophage f1, which facilitates DNA sequencing of the vector and provides a basis for in vitro mutagenesis. To insert a cDNA, pIXY120 is digested with Asp718 which cleaves near the 3' end of the α-factor leader peptide (nucleotide 237) and, for example, NcoI which cleaves in the polylinker. The large vector fragment is then purified and ligated to a DNA fragment encoding the protein to be expressed.

To create a secretion vector for expressing human M-CSFγ, a cDNA fragment including the complete open reading frame encoding hM-CSFγ is cleaved with an appropriate restriction endonuclease proximal to the N-terminus of the mature protein. An oligonucleotide or oligonucleotides are then synthesized which are capable of ligation to the 5' and 3' ends of the hM-CSFγ fragment, regenerating any codons deleted in isolating the fragment, and also providing cohesive termini for ligation to pIXY120 to provide a coding sequence located in frame with respect to an intact α-factor leader sequence.

The resulting expression vectors are then purified and employed to transform a diploid yeast strain of *S. cerevisiae* (XV2181) by standard techniques, such as those disclosed in EPA 0165654, selecting for tryptophan prototrophs. The resulting transformants are cultured for expression of an hM-CSFγ protein as a secreted or extracted product. Cultures to be assayed for hM-CSFγ expression are grown in 20–50 ml of YPD medium (1% yeast extract, 2% peptone, 1% glucose) at 37° C. to a cell density of $1-5 \times 10^8$ cells/ml. To separate cells from medium, cells are removed by centrifugation and the medium filtered through a 0.45μ cellulose acetate filter prior to assay. Supernatants produced by the transformed yeast strain, or extracts prepared from disrupted yeast cells, are assayed for the presence of hG-CSFγ using binding assays as described above.

We claim:

1. An isolated DNA sequence comprising a nucleotide sequence encoding a functional biologically active human M-CSFγ protein.

2. An isolated DNA sequence according to claim 1, selected from the group consisting of:
   (a) cDNA clones having the nucleotide sequence of the coding region of M-CSFγ plasmid pDCCSFγ;
   (b) DNA sequences capable of hybridization to the clones of (a) under moderately stringent conditions and which encode functional biologically active M-CSFγ proteins; and
   (c) DNA sequences which are degenerate as a result of the genetic code to the DNA sequences defined in (a) and (b) and which encode functional biologically active M-CSFγ proteins.

3. An isolated DNA sequence according to claim 1, wherein the DNA sequence encodes an M-CSFγ protein which comprises the sequence of amino acids 33–363 of FIG. 2 and does not include the sequence of amino acids 364–480 of FIG. 2.

4. An isolated DNA sequence according to claim 1, wherein the DNA sequence comprises the sequence of nucleotides 97–1090 of FIG. 2 and does not include the sequence of nucleotides 1091–1438 of FIG. 2.

5. An isolated DNA sequence according to claim 1, wherein the DNA sequence encodes a sequence of amino acids consisting essentially of the sequence of amino acids of M-CSFγ depicted in FIG. 2.

6. An isolated DNA sequence according to claim 1, wherein the DNA sequence consists essentially of the sequence of nucleotides encoding M-CSFγ depicted in FIG. 2.

7. A recombinant expression vector comprising a DNA sequence according to claim 1.

8. A recombinant expression vector comprising a DNA sequence according to claim 2.

9. A recombinant expression vector comprising a DNA sequence according to claim 3.

10. A recombinant expression vector comprising a DNA sequence according to claim 4.

11. A recombinant expression vector comprising a DNA sequence according to claim 5.

12. A recombinant expression vector comprising a DNA sequence according to claim 6.

13. A process for preparing a mammalian M-CSFγ protein comprising culturing a suitable host cell comprising a vector according to claim 7 under conditions promoting expression.

14. A process for preparing a human M-CSFγ protein comprising culturing a suitable host cell comprising a vector according to claim 11 under conditions promoting expression.

15. A process for preparing a mammalian M-CSFγ protein comprising culturing a suitable host cell comprising a vector according to claim 8 under conditions promoting expression.

16. A process for preparing a mammalian M-CSFγ protein comprising culturing a suitable host cell comprising a vector according to claim 9 under conditions promoting expression.

17. A process for preparing a mammalian M-CSFγ protein comprising culturing a suitable host cell comprising a vector according to claim 10 under conditions promoting expression.

18. A process for preparing a mammalian M-CSFγ protein comprising culturing a suitable host cell comprising a vector according to claim 12 under conditions promoting expression.

* * * * *

UNITED STATES PATENT AND TRADEMARK OFFICE
CERTIFICATE OF CORRECTION

PATENT NO. : 5,171,675

DATED : December 15, 1992

INVENTOR(S) : Douglas P. Cerretti, et al.

It is certified that error appears in the above-identified patent and that said Letters Patent is hereby corrected as shown below:

At Column 3, line 25, delete [of] and insert -- or --.
At Column 19, line 26, please insert an -- r -- in "standed".

Column 20:

In Claim 1, please insert -- c -- before "DNA".

Signed and Sealed this

Twenty-first Day of December, 1993

Attest:

BRUCE LEHMAN

Attesting Officer    Commissioner of Patents and Trademarks